United States Patent [19]

Bundy

[11] 4,349,690

[45] Sep. 14, 1982

[54] 9-DEOXY-9-METHYLENE-6-KETO-PGE-TYPE COMPOUNDS

[75] Inventor: Gordon L. Bundy, Portage, Mich.

[73] Assignee: The Upjohn Company, Kalamazoo, Mich.

[21] Appl. No.: 256,624

[22] Filed: Apr. 23, 1981

[51] Int. Cl.$^3$ ............................................. C07C 177/00

[52] U.S. Cl. .................... 560/121; 260/404; 260/405; 560/45; 260/408; 260/410; 560/50; 260/410.5; 260/410.9 R; 560/53; 260/415; 260/409; 560/108; 260/405 D; 542/426; 560/118; 542/429; 546/226; 562/455; 546/284; 546/285; 562/465; 546/309; 546/314; 562/500; 546/316; 546/337; 562/503; 546/342; 544/176; 568/330; 544/391; 549/78; 568/367; 549/79; 424/248.54; 568/379; 424/250; 424/263; 568/380; 424/267; 424/274; 564/80; 424/275; 424/285; 564/88; 424/308; 424/317; 564/95; 424/318; 424/320; 564/98; 424/321; 424/324; 564/99; 424/325; 424/330; 564/123; 424/331; 548/517; 564/158; 548/530; 549/465; 564/166; 549/494; 549/499; 564/169; 549/501; 564/185; 564/186; 564/188; 564/189; 564/217; 564/219; 564/336; 564/443; 564/453; 260/239 BF

[58] Field of Search ................... 560/121, 118, 50, 53, 560/108, 45; 562/503, 463, 500, 455; 568/367, 330, 379, 380; 564/188, 158, 219, 123, 185, 80, 98, 88, 336, 189, 109, 217, 166, 186, 95, 99, 453, 443; 260/404, 408, 410.5, 413, 464, 326.45, 326.2, 347.4, 347.8, 404.5, 410, 410.9 R, 465 D, 239 BF, 326.47, 347.3, 347.7, 345.7 P, 345.8 P, 345.9 P; 542/429, 426; 546/284, 309, 226, 316, 285, 342, 314, 337; 544/176, 391; 549/78, 79

[56] References Cited

U.S. PATENT DOCUMENTS 4,124,601 11/1978 Smith ........................... 260/346.22

Primary Examiner—Robert Gerstl
Attorney, Agent, or Firm—Lawrence T. Welch

[57] ABSTRACT

The present invention provides novel 9-deoxy-9-methylene-6-keto-PGE derivatives which are useful for platelet aggregation inhibition and gastric cyctoprotection.

5 Claims, No Drawings

9-DEOXY-9-METHYLENE-6-KETO-PGE-TYPE COMPOUNDS

BACKGROUND OF THE INVENTION

The present invention provides novel compositions of matter. This invention further provides novel processes for preparing these compositions of matter. The present invention provides novel 9-deoxy-9-methylene-6-keto-PGE type compounds. 6-Keto-PGE-type compounds from which the compounds of this invention are derived are known in the art and are structural and pharmacological analogs of the prostaglandins.

The prostaglandins are a family of 20 carbon atom fatty acids, being structural derivatives of prostanoic acid, which exhibit useful activity in a wide variety of biological systems. Accordingly, such prostaglandins represent useful pharmacological agents in the treatment and prevention of a wide variety of disease conditions. The term "PG-type compounds" is used to describe structural analogs of the prostaglandins. For a fuller discussion of the prostaglandins, see Bergstrom, et al., Pharmacol. Rev. 20: 1 (1968) and references cited therein.

Similarly, the 6-keto-PGE type compounds from which the compounds of the present invention are derived exhibit useful activity in a wide variety of biological systems. They also represent useful pharmacological agents in the treatment and prevention of a wide variety of these disease conditions.

The compounds of the present invention are also useful for inhibiting gastric secretion, for curing and preventing duodenal ulcers, for preventing or treating gastrointestinal cell damage caused by the use of other pharmacological agents, for decreasing blood platelet adhesion, and inhibiting blood platelet aggregation and thrombosis formation induced by various physical and chemical stimuli.

PRIOR ART

The known 6-keto-PGE type compounds are disclosed in U.S. Pat. Nos. 4,215,142; 4,205,178, and 4,223,157.

SUMMARY OF THE INVENTION

The present invention provides a compound of the formula I, wherein $X_1$ is:
  (1) —$COOR_1$, wherein $R_1$ is
    (a) hydrogen,
    (b) ($C_1$–$C_{12}$)alkyl,
    (c) ($C_3$–$C_{10}$)cycloalkyl,
    (d) ($C_7$–$C_{12}$)aralkyl,
    (e) phenyl, optionally substituted with one, 2 or 3 chloro or ($C_1$–$C_3$)alkyl,
    (f) phenyl substituted in the para position by
      (i) —NH—CO—$R_{25}$,
      (ii) —CO—$R_{26}$,
      (iii) —O—CO—$R_{24}$, or
      (iv) —CH=N—NH—CO—$NH_2$ wherein $R_{25}$ is methyl, phenyl, acetamidophenyl, benzamidophenyl, or —$NH_2$; $R_{26}$ is methyl, phenyl, —$NH_2$, or methoxy; and $R_{24}$ is phenyl or acetamidophenyl; inclusive, or
    (g) a pharmacologically acceptable cation;
  (2) —$CH_2OH$,
  (3) —$COL_4$, wherein $L_4$ is
    (a) amino of the formula —$NR_{21}R_{22}$, wherein $R_{21}$ and $R_{22}$ are
      (i) hydrogen,
      (ii) ($C_1$–$C_{12}$)alkyl,
      (iii) ($C_3$–$C_{10}$)cycloalkyl,
      (iv) ($C_7$–$C_{12}$)aralkyl,
      (v) phenyl, optionally substituted with one, 2 or 3 chloro, ($C_1$–$C_3$)alkyl, hydroxy, carboxy, ($C_2$–$C_5$)alkoxycarbonyl, or nitro,
      (vi) ($C_2$–$C_5$)carboxyalkyl,
      (vii) ($C_2$–$C_5$)carbamoylalkyl,
      (viii) ($C_2$–$C_5$)cyanoalkyl,
      (ix) ($C_3$–$C_6$)acetylalkyl,
      (x) ($C_7$–$C_{11}$)benzoylalkyl, optionally substituted by one, 2 or 3 chloro, ($C_1$–$C_3$)alkyl, hydroxy, ($C_1$–$C_3$)alkoxy, carboxy, ($C_2$–$C_5$)alkoxycarbonyl, or nitro,
      (xi) pyridyl, optionally substituted by one, 2, or 3 chloro ($C_1$–$C_3$)alkyl, or ($C_1$–$C_3$)alkoxy,
      (xii) ($C_6$–$C_9$)pyridylalkyl optionally substituted by one, 2 or 3 chloro, ($C_1$–$C_3$)alkyl, hydroxy, or ($C_1$–$C_3$)alkyl,
      (xiii) ($C_1$–$C_4$)hydroxyalkyl,
      (xiv) ($C_1$–$C_4$)dihydroxyalkyl,
      (xv) ($C_1$–$C_4$)trihydroxyalkyl,
    with the further proviso that not more than one of $R_{21}$ and $R_{22}$ is other than hydrogen or alkyl,
    (b) cycloamino selected from the group consisting of pyrolidino, piperidino, morpholino, piperazino, hexamethyleneimino, pyrrolino, or 3,4-didehydro piperidinyl optionally substituted by one or 2 ($C_2$–$C_{12}$)alkyl of one to 12 carbon atoms, inclusive;
    (c) carbonylamino of the formula —$NR_{23}COR_{21}$, wherein $R_{23}$ is hydrogen or ($C_1$–$C_4$)alkyl and $R_{21}$ is other than hydrogen, but otherwise as defined above,
    (d) sulfonylamino of the formula —$NR_{23}SO_2R_{21}$, wherein $R_{21}$ and $R_{23}$ are as defined in (c),
  (4) —$CH_2NL_2L_3$, wherein $L_2$ and $L_3$ are hydrogen or ($C_1$–$C_4$)alkyl, being the same or different, or the pharmacologically acceptable acid addition salts thereof when $X_1$ is —$CH_2NL_2L_3$;
wherein $Z_1$ is:
  (1) —$CH_2$—($CH_2$)$_f$—$C(R_2)_2$, wherein $R_2$ is hydrogen or fluoro and f is zero, one, 2 or 3,
  (2) trans—$CH_2$—CH=CH—,
  (3) —(Ph)—($CH_2$)$_g$—, wherein (Ph) is 1,2-, 1,3-, or 1,4-phenylene and g is zero, one, 2 or 3;
wherein $R_8$ is:
  hydrogen, hydroxy, hydroxymethyl, —$OR_{10}$ or —$CH_2OR_{10}$, wherein $R_{10}$ is an acid-hydrolyzable protecting group;
wherein $Y_1$ is:
  trans—CH=CH—, cis—CH=CH—, —$CH_2CH_2$— or —C≡C—;
wherein $M_1$ is $\alpha$-$OR_{12}$:$\beta$-$R_5$ or $\alpha$-$R_5$:$\beta$-$OR_{12}$, wherein $R_5$ is hydrogen or methyl and $R_{12}$ is hydrogen or methyl, with the proviso that $R_{12}$ is methyl only when $R_5$ is hydrogen;
wherein $L_1$ is $\alpha$-$R_3$:$\beta$-$R_4$, $\alpha$-$R_4$:$\beta$-$R_3$, or a mixture of $\alpha$-$R_3$:$\beta$-$R_4$ and $\alpha$-$R_4$:$\beta$-$R_3$, wherein $R_3$ and $R_4$ are hydrogen, methyl, or fluoro, being the same or different, with the proviso that one of $R_3$ and $R_4$ is fluoro only when the other is hydrogen or fluoro;
wherein $R_7$ is:
  (1) —($CH_2$)$_m$—$CH_3$, wherein m is an integer from one to 5, inclusive;

(2) phenoxy optionally substituted by one, two or three chloro, fluoro, trifluoromethyl, $(C_1-C_3)$alkyl, or $(C_1-C_3)$alkoxy, with the proviso that not more than two substituents are other than alkyl;
(3) phenyl, benzyl, phenylethyl, or phenylpropyl optionally substituted on the aromatic ring by one, two or three chloro, fluoro, trifluoromethyl, $(C_1-C_3)$alkyl, or $(C_1-C_3)$alkoxy, with the proviso that not more than two substituents are other than alkyl;
(4) cis—CH=CH—CH$_2$—CH$_3$;
(5) —(CH$_2$)$_2$—CH(OH)—CH$_3$; or
(6) —(CH$_2$)$_3$—CH=C(CH$_3$)$_2$;
(7) cyclopentyl, optionally substituted in the 3 position by $(C_1-C_4)$alkyl;
(8) cyclohexyl optionally substituted by $(C_1-C_4)$alkyl,
(9) —C(R$_3$R$_4$)—(CH$_2$)$_n$—CH$_2$R$_{14}$ wherein R$_3$ and R$_4$ are as defined above (in L$_1$), n is an integer from 1 to 4 and R$_{14}$ is hydrogen or 1-4C alkyl;

wherein —C(L$_1$)—R$_7$ taken together is
(1) cyclopentyl optionally substituted in the 3 position by $(C_1-C_4)$alkyl,
(2) cyclohexyl optionally substituted by $(C_1-C_4)$alkyl,
(3) 2-(2-furyl)ethyl,
(4) 2-(3-thienyl)ethoxy, or
(5) 3-thienyloxymethyl.

Examples of phenyl esters substituted in the para position (i.e., X$_1$ is —COOR$_1$, R$_1$ is p-substituted phenyl) include p-acetamidophenyl ester, p-benzamidophenyl ester, p-(p-acetamidobenzamido)phenyl ester, p-(p-benzamidobenzamido)phenyl ester, p-amidocarbonylamidophenyl ester, p-acetylphenyl ester, p-benzylphenyl ester, p-amidocarbonylphenyl ester, p-methoxycarbonylphenyl ester, p-benzoyloxyphenyl ester, p-(p-acetamidobenzoyloxy)phenyl ester and p-hydroxybenzaldehyde semicarbazone ester.

Examples of novel amides herein (i.e., X$_1$ is COL$_4$) include the following:
(1) Amides within the scope of alkylamido groups of the formula —NR$_{21}$R$_{22}$ are methylamide, ethylamide, n-propylamide, n-butylamide, n-pentylamide, n-hexylamide, n-heptylamide, n-octylamide, n-nonylamide, n-decylamide, n-undecylamide, and n-dodecylamide, and isomeric forms thereof. Further examples are dimethylamide, diethylamide, di-n-propylamide, di-n-butylamide, methylethylamide, methylpropylamide, methylbutylamide, ethylpropylamide, ethylbutylamide and propylbutylamide. Amides within the scope of cycloalkylamido are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, N-ethyl-N-cyclohexylamide, dicyclopentylamide, and dicyclohexylamide. Amides within the scope of aralkylamido are benzylamide, 2-phenylethylamide, 2-phenylethylamide, N-methyl-N-benzylamide, and dibenzylamide. Amides within the scope of substituted phenylamino and p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanalide, m-methylanilide, p-ethylanilide, t-butylanilide, p-carboxyanilide, p-methoxycarbonylanilide, o-carboxyanilide and o-hydroxyanilide. Amides within the scope of carboxyalkylamido are carboxyalkylamido, carboxymethylamide, carboxyethylamide, carboxypropylamide, and carboxybutylamide. Amides within the scope of the carbamoylalkylamido are carbamoylmethylamide, carbamoylethylamide, carbamoylpropylamide, and carbamoylbutylamide. Amides within the scope of cyanoalkylamido are cyanomethylamide, cyanoethylamide, cyanopropylamide and cyanobutylamide. Amides within the scope of acetylalkylamido are acetylmethylamide, acetylethylamide, acetylpropylamide, and acetylbutylamide. Amides within the scope of benzoylalkylamido are benzoylmethylamide, benzoyethylamide, benzoylpropylamide, and benzoylbutylamide. Amides within the scope of substituted benzoylalkylamido are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoylbenzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5-trimethoxybenzoylethylamide, p-hydroxymethylbenzoylethylamide, p-methylbenzoylethylamide, m-methylbenzoylethylamide, p-ethylbenzoylethylamide, t-butyl-benzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutylamide, m-methylbenzoylbutylamide, p-ethylbenzoylbutylamide, t-butylbenzoylbutylamide, p-carboxybenzoylbutylamide, m-methoxycarbonylbenzoylbutylamide, o-carboxybenzoylbutylamide, o-hydroxybenzoylmethylamide. Amides within the scope of pyridylamido are α-pyridylamide, β-pyridylamide, and γ-pyridylamide. Amides within the scope of substituted pyridylamido are 4-methyl-α-pyridylamide, 4-methyl-β-pyridylamide, 4-chloro-α-pyridylamide, and 4-chloro-β- pyridylamide. Amides within the scope of pyridylalkylamido are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamido are 4-methyl-α-pyridylmethylamide, 4-methyl-β-pyridylmethylamide, 4-chloropyridylmethylamide, 4-chloro-β-pyridylmethylamide, 4-methyl-α-pyridylethylamide, 4-methyl-β-pyridylethylamide, 4-chloropyridethylamide, 4-chloro-β-pyridylethylamide, 4-methyl-α-pyridylpropylamide, 4-methyl-β-pyridylpropylamide, 4-chloro-pyridylpropylamide, 4-chloro-β-pyridylpropylamide, 4-methyl-β-pyridylbutylamide, 4-methyl-α-pyridylbutylamide, 4-chloropyridylbutylamide, 4-chloro-β-pyridylbutylamide, 4-methyl-β-pyridylbutylamide. Amides within the scope of hydroxyalkyl are hydroxymethylamide, α-hydroxyethylamide, β-hydroxyethylamide, α-hydroxypropylamide, β-hydroxypropylamide, γ-hydroxypropylamide, 1-(hydroxymethyl)ethylamide, 1-(hydroxymethyl)propylamide, (2-hydroxymethyl)propylamide, and α,α-dimethyl-β-hydroxy ethylamide. Amides within the scope of dihydroxyalkylamide are dihydroxymethylamide, α,α-dihydroxyethylamide, α,β-dihydroxyethylamide, β,β-dihydroxyethylamide, α,α-dihydroxypropylamide, α,β-dihydroxypropylamide, α,γ-dihydroxypropylamide, β,β-dihydroxypropylamide, β,γ-dihydroxypropylamide, γ,γ-dihydroxypropylamide, 1-(hydroxymethyl)-2-hydroxyethylamide, 1-(hydroxymethyl)-1-hydroxyethylamide, α,α-dihydroxybutylamide, α,β-dihydroxybutylamide, α,γ-dihydroxybutylamide, α,δ-dihydroxybutylamide, α,δ-dihydroxybutylamide, β,β-dihydroxybutylamide, β,γ-dihydroxybutylamide, β,δ-dihydroxybutylamide, γ,γ-dihydroxybutylamide, γ,δ-dihydroxybutylamide, δ,δ-dihydroxybutylamide, and 1,1-bis(hydroxymethyl)ethylamide. Amides within the scope of trihydroxyalkylamino are tris(hydroxymethyl)methylamide and 1,3-dihydroxy-2-hydroxymethylpropylamide.

(2) Amides within the scope of the cycloamido groups described above are pyrrolidylamide, piperidylamide, morpholinylamide, hexamethyleneiminylamide, piperazinylamide, pyrrolinylamide, and 3,4-didehydropiperidinylamide.

(3) Amides within the scope of carbonylamido of the formula —NR$_{23}$COR$_{21}$ are methylcarbonylamide, ethylcarbonylamide, phenylcarbonylamide, and benzylcarbonylamide. Amides within the scope of sulfonylamido of the formula —NR$_{21}$SO$_2$R$_{21}$ are methylsulfonylamide, ethylsulfonylamide, phenylsulfonylamide, p-tolylsulfonylamide, benzylsulfonylamide.

(4) Hydrazines within the scope of the above hydrazino groups are hydrazine, N-aminopiperidine, benzoylhydrazine, N-aminomorpholine, 2-hydroxyethylhydrazine, methylhydrazine, 2,2,2-hydroxyethylhydrazine and p-carboxyphenylhydrazine.

The carbon atom content of various hydrocarbon-containing moieties is indicated by a prefix designation the minimum and maximum number of carbon atoms in the moiety, i.e., the prefix (C$_i$–C$_j$) indicates a moiety of the integer "i" to the integer "j" carbon atoms, inclusive. Thus (C$_1$–C$_3$)alkyl refers to alkyl of one to 3 carbon atoms, inclusive, or methyl, ethyl, propyl, and isopropyl.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of substituted benzyl, phenylethyl, or phenylpropyl are (o-, m-, or p-)tolyl, (o-, m-, or p-)ethylphenyl, 2-ethyl-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-,4-,5- or 6-)chloro-o-tolyl, 4-chloro-2-propylphenyl, 2-isopropyl-4-chlorophenyl, 4-chloro-3,5-xylyl, (2,3-, 2,4- 2,5- 2,6- or 3,5-)dichlorophenyl, 4-chloro-3-fluorophenyl, (3- or 4-)chloro-2-fluorophenyl, (o-, m-, or p-)trifluoromethylphenyl, (o-, m-, or p-)ethoxyphenyl, (4- or 5-)chloro-2-methoxyphenyl, and 2,4-dichloro-(5- or 6-)methylphenyl.

With regard to the divalent substituents described above (e.g., L$_1$ and M$_1$), these divalent radicals are defined as α-R$_i$:β-R$_j$, wherein R$_i$ represents the substituent of the divalent moiety in the alpha configuration with respect to the ring and R$_j$ represents the substituent of the divalent moiety in the beta configuration with respect to the plane of the ring. Accordingly, when M$_1$ is defined as α-OH:β-H, the hydroxy of the M$_1$ moiety is in the alpha configuration, and the hydrogen substituent is in the beta configuration.

These novel compounds are useful whenever it is desired to inhibit platelet aggregation, reduce the adhesive character of platelets, and remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants of prolonged action. For rapid response especially in emergency situations, the intravenous route of administration is preferred. Doses in the range about 1 μg/kg to about 100 mg/kg of body weight per day are used, the exact dose depending on the age, weight, and condition of the patient or animal, and on the frequency and route of administration.

These novel compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg per liter of circulating fluid. It is especially useful to use these compounds in laboratory animals, e.g., cats, dogs, rabbits, monkeys, and rats, for these purposes in order to develop new methods and techniques for organ and limb transplants.

The prostaglandin analogs of the present invention are useful in mammals, including humans and certain useful animals, e.g., dogs and pigs, to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 μg to about 500 μg/kg of body weight per minute, or in a total daily dose by injection or infusion in the range about 0.1 to about 20 mg/kg of body weight per day, the exact dose depending on the age, weight, and condition of the patient or animal, and on the frequency and route of administration.

These compounds are also useful in reducing the undesirable gastrointestinal effects resulting from systemic administration of anti-inflammatory prostaglandin synthetase inhibitors, and are used for the purpose by concomitant administration of the prostaglandin and the anti-inflammatory prostaglandin synthetatase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including $PGE_1$, $PGE_2$, $PGE_3$, 13,14-dihydro-$PGE_1$, and the corresponding 11-deoxy-PGE and PGA compounds. The compounds of the present invention are useful, for example, in reducing the undesirable gastrointestinal effects resulting from systemic administration of indomethacin, phenylbutazone, and aspirin. These are substances specifically mentioned in Partridge et al., as non-steroidal, anti-inflammatory agents. These are also known to be prostaglandin synthetase inhibitors.

The prostaglandin analog is administered along with the anti-inflammatory prostaglandin synthetase inhibitor either by the same route of administration or by a different route. For example, if the anti-inflammatory substance is being administered orally, the prostaglandin is also administered orally, or alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally, or, alternatively, orally or, in the case of women, vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex, and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experienced the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of prostalandin to reduce and then substantially to eliminate those undesirable effects.

When $X_1$ is —$COOR_1$, the novel compounds are used for the purposes described above in the free acid form, in ester form, and in the pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of the novel compounds of this invention compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, glactamine, N-methylglycamine, N-methylglucosamine, ephedrine, phenylephrine, epinephrine, procaine, and the like. Further useful amine salts are the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

Certain compounds of the present invention are preferred to obtain the optimal combination of biological response, specificity, potency, and duration of activity. Thus, compounds of the formula I, wherein $X_1$ is $-CO_2H$ or $-CO_2CH_3$, $Z_1$ is $-(CH_2)_3-$, $R_3$ and $R_4$ are hydrogen or methyl, and $R_7$ is $-(CH_2)_3CH_3$, $-(CH_2)_4CH_3$, cyclohexyl, cyclopentyl, or substituted cyclopentyl, are preferred. Compounds which satisfy one or more of these preferences are more preferred and compounds wherein all of the above variables are a preferred substituent are most preferred.

The compounds of the present invention are prepared by selective sulfoximine addition at carbon number 9 from the corresponding 6,9-diketones of the prior art, which are disclosed in U.S. Pat. Nos. 4,215,142; 4,205,178; and 4,223,157.

A more general procedure is depicted in Chart A.

In Chart A, $Y_1$, $Z_1$, $X_1$, $M_1$, $L_1$, $R_7$ and $R_8$ are as defined above. $M_2$ is $\alpha\text{-}OR_{18}\text{:}\beta\text{-}R_5$, $\alpha\text{-}R_5\text{:}\beta\text{-}OR_{18}$, $\alpha\text{-}OCH_3\text{:}\beta\text{-}R_5$, or $\alpha\text{-}R_5\text{:}\beta\text{-}OCH_3$. $X_2$ IS coextensive with $X_1$ except when $X_1$ is $COOR_1$, $R_1$ is not hydrogen. $R_{18}$ is a silyl protecting group of the formula $-Si(G_1)_3$. $G_1$ is alkyl of one to 4 carbon atoms, cycloalkyl of 3 to 10 carbon atoms, inclusive, aralkyl of 7 to 12 carbon atoms, inclusive, phenyl, or phenyl substituted with one or 2 fluoro, chloro, or alkyl of one to 4 carbon atoms, with the proviso that in a $-Si(G_1)_3$ moiety the various $G_1$'s are the same or different and at least one $G_1$ is hindered (such as tert-butyl). Silyl groups within the scope of $-Si(G_1)_3$ include dimethylphenylsilyl, triphenylsilyl, t-butyldimethylsilyl, or methylphenylbenzylsilyl. With regard to $G_1$, examples of alkyl are methyl, ethyl, propyl, isobutyl, butyl, sec-butyl, tert-butyl, pentyl, and the like. Examples of aralkyl are benzyl, phenethyl, α-phenylethyl, 3-phenylpropyl, α-maphthylmethyl, and 2-(α-maphthyl)ethyl. Examples of phenyl substituted with halo or alkyl are p-chlorophenyl, m-fluorophenyl, o-tolyl, 2,4-dichlorophenyl, p-tert-butylphenyl, 4-chloro-2-methylphenyl, and 2,4-dichloro-3-methylphenyl. Tert-butyldimethylsilyl is most preferred as a silylating agent.

These silyl groups are known in the art. See for example, Pierce "Silylating of Organic Compounds," Pierce Chemical Company, Rockford Ill. (1968). When silylated products of the charts below are intended to be subjected to chromatographic purification, then the use of silyl groups known to be unstable to chromatography is to be avoided. Further, when silyl groups are to be introduced selectively, silylating agents which are readily available and known to be useful in selective silylations are employed. For example, triphenylsilyl and t-butyldimethylsilyl groups are employed when selective introduction is required. A particularly useful silyl group for this purpose is t-butyldimethylsilyl, although other silyl groups are likewise employed.

The protective groups within the scope of $R_{10}$ are any group which replaces a hydroxy hydrogen and is neither attacked by nor is as reactive to the reagents used in the transformations used herein as a hydroxy is and which is subsequently replaceable by acid hydrolysis with hydrogen in the preparation of the prostaglandin-type compounds. Several such protective groups are known in the art, e.g., tetrahydropyranyl and substituted tetrahydropyranyl. See for reference E. J. Corey, Proceedings of the Robert A. Welch Foundation Conferences on Chemical Research, XII Organic Synthesis, pgs. 51–79 (1969). Those blocking groups which have been found useful include:

(a) tetrahydropyranyl;
(b) tetrahydrofuranyl; and
(c) a group of the formula $-C(OR_{11})(R_{12})-CH(R_{13})(R_{14})$, wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted wityh one to 3 alkyl of one to 4 carbon atoms, inclusive, wherein $R_{12}$ and $R_{13}$ are alkyl of one to 4 carbon atoms, inclusive, phenyl, phenyl substituted with one, 2, or 3 alkyl of one to 4 carbon atoms, inclusive, or when $R_{12}$ and $R_{13}$ are taken together $-(CH_2)_a-$ or when $R_{12}$ and $R_{13}$ are taken together $-(CH_2)_b-O-(CH_2)_c-$, wherein a is 3, 4, or 5 and b is one, 2 or 3, and c is one, 2, or 3, with the proviso that b plus c is 2, 3, or 4, with the further proviso that $R_{12}$ and $R_{13}$ may be the same or different, and wherein $R_{14}$ is hydrogen or phenyl.

When the blocking group $R_{10}$ is tetrahydropyranyl, the tetrahydropyranyl ether derivative of any hydroxy moieties of the CBA-type intermediates herein is obtained by reaction of the hydroxy-containing compound with 2,3-dihydropyran in an inert solvent, e.g., dichloromethane, in the presence of an acid condensing agent such as p-toluenesulfonic acid or pyridine hydrochloride. The dihydropyran is used in large stoichiometric excess, preferably 4 to 100 times the stiochiometric amount. The reaction is normally complete in less than an hour at 20°–50° C.

When the protective group is tetrahydrofuranyl, 2,3-dihydrofuran is used, as described in the preceding paragraph, in place of the 2,3-dihydropyran.

When the protective group is of the formula $-C(OR_{11})(R_{12})-CH-(R_{13})(R_{14})$, wherein $R_{11}$, $R_{12}$, $R_{13}$, and $R_{14}$ are as defined above; a vinyl ether or an unsaturated cyclic or heterocyclic compound, e.g., 1-cyclohexen-1-yl methyl ether, or 5,6-dihydro-4-methoxy-2H-pyran is employed. See C. B. Reese, et al., Journal of the Chemical Society 86, 3366 (1967). The reaction conditions for such vinyl ethers and unsaturated compounds are similar to those for dihydropyran above.

The protective groups as defined by $R_{10}$ and $R_{18}$ are removed by mild acidic hydrolysis. For example, by reaction with (1) hydrochloric acid in methanol; (2) a mixture of acetic acid, water, and tetrahydrofuran, or (3) aqueous citric acid or aqueous phosphoric acid in tetrahydrofuran, at temperatures below 55° C., hydrolysis of the blocking group is achieved.

A protected 6-keto-PGF type compound of the formula XI is prepared from the corresponding 5-iodo PGI type compound in the manner disclosed in the U.S. patents cited above, for example by treating the iodoether with t-butyldimethylsilyl chloride and imidazole and then with 1,5-diazobicyclo[5.4.0]undec-5-ene (DBU). (The 5-iodo ethers of formula X are known and are disclosed, for example, in U.S. Pat. No. 4,158,667.)

The formula XI compound is then oxidized to the corresponding diketo compound using any of the known methods, e.g., using any of the following reagents:

Jones Reagent (acidified chromic acid, see Journal of American Chemical Society, 39 (1946)), Collins Reagent (chrominium trioxide in pyridine, see collins, et al., Tetrahedron Lett., 3363 (1968)), mixtures of chromium trioxide in pyridine, see Journal of the American Chemical Society 75, 422 (1953)), tert-butyl chromate in pyridine (see Biological Chemistry Journal, 84 195 (1962)), mixtures of sulfur trioxide in pyridine and dimethyl sulfoxide (see Journal of the American Chemical Society, 89, 5505 (1967)), and mixtures of dicyclohexylcarbodiimide and dimethylsulfoxide (see Journal of the American Chemical Society, 87, 5661 (1965)).

The formula XII diketone is then converted to the formula XIII methylene analog by sulfoximine addition at the 9-keto position. For example, methylphenyl-N-methylsulfoximine is treated with methylmagnesium chloride to form the sulfoximine anion which is added to a solution of the diketone. This $\beta$-hydroxysulfoximine intermediate product is then treated with an aluminum amalgam to yield the formula XIII protected analog. This sulfoximine addition chemistry is known and is disclosed, for example, in C. R. Johnson, et al., J. Am. Chem. Soc. 95:6462 (1973).

The protective groups are removed by any of the known methods, for example treatment with acetic acid, to yield the formula XIV product.

For compounds wherein $X_1$ is —COOH, the corresponding ester is converted to its free acid by any of the known methods, e.g., treatment with aqueous potassium hydroxide. Alternatively, the corresponding acid may be obtained by enzymatic hydrolysis using *Plexaura homomalla*-derived esterase. See, for example W. P. Schneider, et al., J. Am. Chem. Soc. 99:1222 (1977).

DESCRIPTION OF THE PREFERRED EMBODIMENTS

The present invention is more fully understood by the Examples set out below.

EXAMPLE 1

9-Deoxo-9-methylene-6-keto-PGE$_1$, methyl ester (Formula I, $X_1$ is COOR$_1$, R$_1$ is methyl, R$_8$ is OH, Z$_1$ is —(CH$_2$)$_3$—, Y$_1$ is trans—CH=CH—, M$_1$ is $\alpha$-OH:$\beta$-H, R$_3$ and R$_4$ are hydrogen, and R$_7$ is —(CH$_2$)$_2$—CH$_3$)

To a stirred solution of 22 g (44.5 mmoles) of Formula X iodoether corresponding to the titled product in 220 ml of Burdick and Jackson dimethylformamide is added 14.74 g (97.81 mmoles) of t-butyldimethylsilyl chloride, followed by 13.31 g (195.7 mmoles) of imidazole. The resulting clear solution is stirred at 25° for 16 hr in an atmosphere of nitrogen, poured into water, ice and brine, and extracted thoroughly with 10% ethyl acetate/hexane. The organic layers are washed twice with water, once with brine, dried over anhydrous magnesium sulfate, filtered through a 1-inch pad of silica on a medium porosity sintered glass funnel, and evaporated. The crude product (28.5 g, 89% of theory) is greater than 95% pure by TLC and is carried on without purification.

TLC analysis yields the following: R$_f$0.64 (25% ethyl acetate/hexane; starting diol had R$_f$ 0.00 on the same plate).

The crude silyl derivative is dissolved in 600 ml of toluene, treated with 35 ml of 1,5-diazabicyclo[5.4.0]undec-5-ene (DBU) and stirred at 45° for 16 hr, and then at 30° for an additional 48 hr. The solution is cooled to 0° and treated with 350 ml of cold 1 M aqueous hydrochloric acid, and the resulting two-phase mixture was stirred vigorously for 15 min at 0°. The mixture is then poured into ice and brine, and extracted with toluene. The extracts are washed with water, aqueous sodium bicarbonate, and brine, and dried over anhydrous magnesium sulfate. The toluene solution is poured onto a column containing 3 kg of silica gel. The column is eluted (approx. 1000 ml fractions) with 25% ethyl acetate/hexane, using vacuum to speed the elution.

Fractions 15–33, homogeneous by TLC, are combined and afford 23 g (95% of theory; 84% from 1) of pure 6-keto-PGF$_1\alpha$ methyl ester, 11,15-bis(t-butyldimethylsilyl ether) of the Formula XI as a viscous, colorless oil.

Spectral analysis yields the following:
Infrared- $\nu$max (neat) 3430, 1740, 1360, 1250, 1120, 1090, 1060, 1000, 970, 840 and 780 cm$^{-1}$;

NMR (CCDl$_3$; TMS): $\delta$ 5.60–5.30 (m, 2H), 4.80–3.60 (s at 3.64 superimposed on m, 6H total), 0.88 (s, 18H) and 0.05 ppm (s, 12H);

Mass spectrum (neat or TMS derivative): Highest peak at m/e 594.4101; calc'd. for C$_{33}$H$_{62}$Si$_2$O$_5$, 594.4136. This peak corresponds to M$^+$—H$_2$O;

TLC (Silica gel GF): R$_f$0.25 (25% ethyl acetate/hexane; the iodoether exhibited R$_f$0.67 on the same plate).

Collins reagent is prepared in the usual manner by adding 24 g of anhydrous chromium trioxide to a stirred solution of 41.3 ml of pyridine in 650 ml of methylene chloride, in a 10° cool water bath. The dark red mixture is then stirred an additional 30 min at 25°. To this stirred solution is added a solution of 23 g (37.58 mmoles) of the 9$\alpha$-hydroxy intermediate prepared in the previous paragraph in 100 ml of methylene chloride, followed immediately by two tablespoons of dry Celite ®. The mixture is stirred at 25° for 40 min, and then poured directly onto a column containing 3 kg of silica gel. The column is eluted rapidly (with the acid of a vacuum) with 25% ethyl acetate/hexane (approx. 1000 ml fractions). Fractions which contain the major less polar product are combined and evaporated, affording 19 g of crude Formula XII diketone, free from the chromium sludge, but still containing several minor, less polar contaminants.

The partially purified product (19 g) is chromatographed on a 3 kg column of silica gel, packed and eluted with 2% acetone/methylene chloride. (The first 8 l were collected in a single container, then 300 ml fractions).

Fractions 2–6 were combined and afforded 2.07 g of the major less polar impurity.

Fractions 31–60 from the above chromatogram yielded 14.2 g of pure 6,9-diketone (62% of theory), which exhibited the following spectral characteristics:

Infrared: $\nu$max (neat) 1740, 1720, 1250, 1160, 1110, 1090, 1000, 970, 940, 840, and 780 cm$^{-1}$;

NMR (CDCl$_3$; TMS): $\delta$ 5.65–5.40 (m, 2H), 4.65–3.80 (m, 2H), 3.64 (s, 3H), 0.88 (s, 18H) and 0.05 ppm (s, 12H);

TLC (Silica gel GF): R$_f$0.50 (30% ethyl acetate/hexane);

Mass spectrum: M+ (found): 610.4110; calc'd. for $C_{32}H_{62}Si_2O_6$, 610.4084; other ions at m/e 595, 579, 553, 535, 521, 478, 453, 447, 407, 215, 143, and 111.

A solution of 4.82 g (28.49 mmoles) of methylphenyl-N-methylsulfoximine in 50 ml of tetrahydrofuran is cooled to 0° under nitrogen and treated dropwise with 10 ml of 2.8 M methylmagnesium chloride (28.0 mmoles) in tetrahydrofuran (methane evolution). After 10 min longer at 0°, the sulfoximine anion solution is cooled to −78° C. and transferred via double ended needle to a stirred, −78° C. solution of 14.2 g (23.28 mmoles) of the Formula XII diketone (prepared in the previous paragraph) in 300 ml of tetrahydrofuran. (The transfer requires 2 min.). After 2 hr at −78°, TLC analysis of an aliquot (aqueous ammonium chloride/ethyl acetate vial workup; 35% ethyl acetate/hexane for the solvent) indicates that 60-70% of the starting material remains. Therefore, another portion of the sulfoximine anion solution is prepared exactly as described above (same amounts) and transferred at −78° to the stirred reaction mixture. After an additional 2 hr at −78°, TLC indicates less than 20% starting material remaining. Saturated aqueous ammonium chloride (100 ml) is added to the −78° reaction mixture, which is then allowed to warm to room temperature. Brine is added and the product is isolated by extraction with 50% ethyl acetate/hexane. The extracts are washed twice with brine, dried over anhydrous magnesium sulfate, and concentrated in vacuo.

The crude product (23 g) is chromatographed on a 3 kg column of silica gel. The column is packed with 30% ethyl acetate/hexane and eluted with 2 l of the same solvent, followed by 25 l of 35% ethyl acetate/hexane (400 ml fractions).

Fractions 7-12 yield 1.50 g of pure starting diketone identified by its IR and NMR spectra.

Fractions 29-50 afford 8.90 g of the desired C-9 β-hydroxysulfoximine intermediate, a mixture of C-9 epimers (55% yield when account is taken of recovered starting material.)

TLC analysis (Silica gel GF) yields the following: $R_f$ 0.18 (major) and 0.16 (minor) (30% ethyl acetate/hexane; the starting diketone exhibits $R_f$ 0.50 on the same plate).

A solution of 8.9 g (11.42 mmoles) of the β-hydroxysulfoximine intermediate from the preceding paragraph in 250 ml of tetrahydrofuran is cooled to 10° and treated with 35 ml of water, 35 ml of acetic acid, and an aluminum amalgam prepared from 10 g of 20 mesh aluminum. The reaction mixture is stirred vigorously at 10°-15° for 1 hr, cooled to 0°, diluted with 300 ml of ethyl acetate, treated with two tablespoons of Celite ®, and filtered through a medium-porosity sintered glass funnel. The filtrate is diluted with 200 ml of hexane, washed with aqueous sodium bicarbonate and brine, dried over anhydrous magnesium sulfate, and concentrated in vacuo.

The crude product is chromatographed on a 1.3 kg column of silica gel, packed and eluted with 10% ethyl acetate/hexane (2300 ml in a single container, and then 100 ml fractions).

Fractions 8-18, homogeneous by TLC, were combined and afforded 5.25 g of pure Formula XIII 9-deoxo-9-methylene derivative of a semi-viscous, colorless oil (75% of theory).

Infrared spectral analysis yields the following:
νmax (neat 1740, 1720, 1655, 1360, 1255, 1245, 1110, 1090, 1000, 970, 840, 780 cm$^{-1}$.

NMR (CDCl$_3$; TMS): δ 5.65-5.42 (m, 2H), 5.00-4.60 (m, 2H), 4.30-3.80 (m, 2H), 3.66 (s, 3H), 0.90 (s, 18H) and 0.06 ppm (s, 12H).

Mass spectrum: M+ (found), 608.4285; calc'd. for $C_{34}H_{64}Si_2O_5$, 608.4292; other ions at m/e 593, 577, 541, 476, 459, 445, 419, 405, 345, 215, 143, 111.

TLC analysis (Silica gel GF) yields the following:

| | | |
|---|---|---|
| 1% | acetone/methylene chloride | 0.30 |
| 3% | 2-propanol/hexane | 0.22 |
| 7% | acetone/hexane | 0.35 |
| 10% | ethyl acetate/hexane | 0.35 |
| 15% | ethyl acetate/hexane, silver nitrate plate | 0.39 |

A solution of 5.05 g of Formula XIII 9-methylene derivative in 100 ml of acetic acid, 40 ml of water and 20 ml of tetrahydrofuran is stirred under nitrogen for 6 hr at 42° C. The reaction mixture is then concentrated to an oil using a high vacuum pump on a rotary evaporator.

The crude product (approx. 90% pure by TLC) is chromatographed on a 150 g column of silica gel, packed with 25% ethyl acetate/hexane, and eluted (23 ml fractions) with 500 ml of 50% ethyl acetate/hexane, 2 l of 80% ethyl acetate/hexane and 1 l of ethyl acetate.

Fractions 51-90 are combined based on their TLC homogeneity (80% ethyl acetate/hexane), and yield 2.74 g of pure Formula XIV 9-deoxo-9-methylene-6-oxo-PGE$_1$, methyl ester, which crystallizes spontaneously (87% of theory). Recrystallization from ethyl acetate/hexane (8 ml/10 ml) affords 1.975 g of a colorless crystalline solid. (The mother liquors—725 mg—crystallizes readily and are saved separately.)

The product has a melting point of 55.1°-56.3° C.
Spectral analysis yields the following:
Infrared: νmax (mull) 3360, 3280, 1735, 1705, 1670, 1660, 1250, 1195, 1175, 1085, 955 and 890 cm$^{-1}$.

NMR (CDCl$_3$; TMS): δ 5.65-5.40 (m, 2H), 5.0-4.80 (m, 1H), 4.80-4.60 (m, 1H), 4.30-3.50 ppm (s at 3.67 superimposed on m, 5H total).

Mass spectrum (TMS derivative): M+ (found), 524.3318; calc'd for $C_{28}H_{52}Si_2O_5$: 524.3353; other ions at m/e 509, 493, 453, 434, 409, 403, 363, 295, 291, 277, 276, 243, 143, and 111.

The carbon:hydrogen ratio is 68.76:9.34.
TLC analysis (silica gel GF) yields the following: $R_f$
0.26 (80/20/1 ethyl acetate/hexane/acetic acid)
0.30 (30/70/1 acetone/methylene chloride/acetic acid)

EXAMPLE 2

9-Deoxo-9-methylene-6-keto-PGE$_1$ (Formula I: $X_1$ is COOR$_1$, R$_1$ is hydrogen, R$_8$ is OH, Z$_1$ is —(CH$_2$)$_3$—, Y$_1$ is trans—CH=CH—, M$_1$ is α-OH:β-H, R$_3$ and R$_4$ are hydrogen, and R$_7$ is —(CH$_2$)$_2$—CH$_3$))

A solution of 2.17 g of methyl ester prepared in Example 1 in 15 ml of methanol is cooled to 0° and treated with 10 ml of aqueous 1 M potassium hydroxide. The reaction mixture is then stirred under nitrogen for 16 hr at 25°, recooled to 0°, diluted with 20 ml of water and 5.1 ml of 2 M sodium bisulfate, poured into ice/brine and extracted with ethyl acetate. The extracts are washed with brine, dried over anhydrous magnesium sulfate, and concentrated in vacuo.

The crude product crystallizes readily on stadning and is recrystallized from ethyl acetate/hexane (15 ml/4 ml), thereby affording 1.93 g of pure 9-deoxo-9-methylene-6-keto-PGE$_1$, as a colorless crystalline solid.

The product has a melting point of 81.9°-83.3° C. Spectral analysis yields the following: $\nu$max (mull) 3260, 3000, 1710, 1655, 1320, 1260, 1070, 970, 890, and 870 cm$^{-1}$.

NMR (CDCl$_3$; TMS): $\delta$6.05 (s, 3H, shifts downfield on cooling), 5.65-5.40 (m, 2H), 5.00-4.80 (m, 1H), 4.80-4.60 (m, 1H), 4.30-3.60 ppm (m, 2H).

Mass spectrum (TMS derivative): M$^+$ (found), 582.3628; calc'd. for C$_{30}$H$_{58}$Si$_3$O$_5$, 582.3662; other ions at m/e 567, 563, 549, 511, 492, 477, 421, 295, 291, 277, 276, 201, 173, 111.

The carbon:hydrogen ratio is 68.69:9.29.

TLC analysis (silica gel GF) yields the following: R$_f$ 0.19 (80/20/1 ethyl acetate/hexane/acetic acid)

0.20 (30/70/1 acetone/methylene chloride/acetic acid).

EXAMPLE 3

9-Deoxo-9-methylene-16,16-dimethyl-6-keto-PGE$_1$ (Formula I, X is COOR$_1$, R$_1$ is hydrogen, Z$_1$ is —(CH$_2$)$_3$—, Y$_1$ is trans—CH=CH—, M$_1$ is $\alpha$-OH:$\beta$-H, R$_3$ and R$_4$ are methyl, and R$_7$ is —(CH$_2$)$_2$—CH$_3$)

Following the procedure of the preceding Examples, the titled compound is prepared from the corresponding 16,16-dimethyl iodoether.

EXAMPLE 4

Following the procedure of the preceding Examples 9-deoxy-9-methylene-6-keto PGE type compounds are prepared exhibiting the following side chain variations:
15-methyl-;
16-methyl-;
16-fluoro-;
16,16-difluoro-;
15-methyl-16,16-difluoro-;
17-phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
15-methyl-17-phenyl-18,19,20-trinor-;
16-methyl-17-phenyl-18,19,20-trinor-;
16,16-dimethyl-17-phenyl-18,19,20-trinor-;
16-fluoro-17-phenyl-18,19,20-trinor-;
16,16-difluoro-17-phenyl-18,19,20-trinor-;
16-phenoxy-17,18,19,20-trinor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
15-methyl-16-phenoxy-17,18,19,20-tetranor-;
16-phenoxy-18,19,20-trinor-;
15-methyl-16-phenoxy-18,19,20-trinor-;
13,14-dihydro-;
15-methyl-13,14-didehydro-;
16-methyl-13,14-didehydro-;
16,16-dimethyl-13,14-didehydro-;
16-fluoro-13,14-didehydro-;
16,16-difluoro-13,14-didehydro-;
17-phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
15-methyl-17-phenyl-18,19,20-trinor-13,14-didehydro-;
16-methyl-17-phenyl-18,19,20-trinor-13,14-didehydro-;
16,16-dimethyl-17-phenyl-18,19,20-trinor-13,14-didehydro-;
16-fluoro-17-phenyl-18,19,20-trinor-13,14-didehydro-;
16,16-difluoro-17-phenyl-18,19,20-trinor-13,14-didehydro-;
16-phenoxy-17,18,19,20-tetranor-13,14-didehydro-;
16-(m-trifluoromethylphenoxy)-17,18,19,20-tetranor-13,14-didehydro-;
16-(m-chlorophenoxy)-17,18,19,20-tetranor-13,14-didehydro-;
15-methyl-16-phenoxy-17,18,19,20-tetranor-13,14-didehydro-;
16-phenoxy-18,19,20-trinor-13,14-didehydro-;
15-methyl-16-phenoxy-18,19,20-trinor-13,14-didehydro-;
16-methyl-16-phenoxy-18,19,20-trinor-13,14-didehydro-;
13,14-dihydro-;
15-,methyl-13,14-dihydro-;
16-methyl-13,14-dihydro-;
16,16-dimethyl-13,14-dihydro-;
16-fluoro-13,14-dihydro-;
16,16-difluoro-13,14-dihydro-;
15-methyl-16,16-difluoro-13,14-dihydro-;
17-phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
15-methyl-17-phenyl-18,19,20-trinor-13,14-dihydro-;
16-methyl-17-phenyl-18,19,20-trinor-13,14-dihydro-;
16,16-dimethyl-17-phenyl-18,19,20-trinor-13,14-dihydro-;
16-fluoro-17-phenyl-18,19,20-trinor-13,14-dihydro-;
16,16-difluoro-17-phenyl-18,19,20-trinor-13,14-dihydro-;
15-methyl-16,16-difluoro-17-phenyl-18,19,20-trinor-13,14-dihydro-;
16-phenoxy-17,18,19,20-tetranor-13,14-dihydro-;
15-methyl-16-phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-phenoxy-18,19,20-trinor-13,14-dihydro-;
15-methyl-16-phenoxy-18,19,20-trinor-13,14-dihydro-;
16-methyl-16-phenoxy-18,19,20-trinor-13,14-dihydro-;
15-dehydro-16-(m-trifluoromethylphenoxy)-17,18,19,20-tetranor-13,14-dihydro-;
15-dehydro-16-(m-chlorophenoxy)-17,18,19,20-tetranor-13,14-dihydro-;
15-dehydro-16-(p-fluorophenoxy)-17,18,19,20-tetranor-13,14-dihydro-;
15-dehydro-16-phenoxy-18,19,20-trinor-13,14-dihydro-;
15-dehydro-16-methyl-16-phenoxy-18,19,20-trinor-13,14-dihydro-;
15-dehydro-16-methyl-16-phenoxy-18,19,20-trinor-; and
15-dehydro-16,16-dimethyl-16-phenoxy-17,18,19,20-tetranor-13,14-dihydro.

All the other compounds falling within the scope of this invention are prepared by these means.

FORMULA

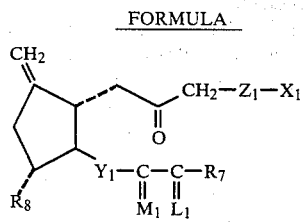

CHART A

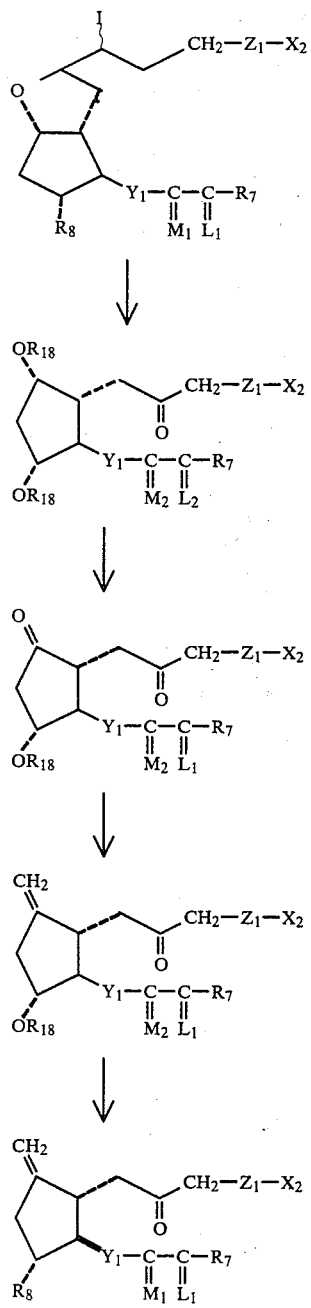

I claim:
1. A compound of the formula I,

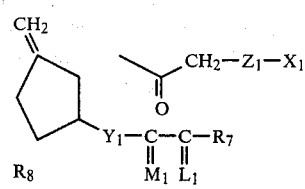

wherein $X_1$ is:
 (1) —$COOR_1$, wherein $R_1$ is
  (a) hydrogen,
  (b) $(C_1-C_{12})$alkyl,
  (c) $(C_3-C_{10})$cycloalkyl,
  (d) $(C_7-C_{12})$aralkyl,
  (e) phenyl, optionally substituted with one, 2 or 3 chloro or $(C_1-C_3)$alkyl,
  (f) phenyl substituted in the para position by
   (i) —NH—CO—$R_{25}$,
   (ii) —CO—$R_{26}$,
   (iii) —O—CO—$R_{24}$, or
   (iv) —CH=N—NH—CO—$NH_2$ wherein $R_{25}$ is methyl, phenyl, acetamidophenyl, benzamidophenyl, or —$NH_2$; $R_{26}$ is methyl, phenyl, —$NH_2$, or methoxy; and $R_{24}$ is phenyl or acetamidophenyl; inclusive, or
  (g) a pharmacologically acceptable cation;
 (2) —$CH_2OH$,
 (3) —$COL_4$, wherein $L_4$ is
  (a) amino of the formula —$NR_{21}R_{22}$, wherein $R_{21}$ and $R_{22}$ are
   (i) hydrogen,
   (ii) $(C_1-C_{12})$alkyl,
   (iii) $(C_3-C_{10})$cycloalkyl,
   (iv) $(C_7-C_{12})$aralkyl,
   (v) phenyl, optionally substituted with one, 2 or 3 chloro, $(C_1-C_3)$alkyl, hydroxy, carboxy, $(C_2-C_5)$ alkoxycarbonyl, or nitro,
   (vi) $(C_2-C_5)$carboxyalkyl,
   (vii) $(C_2-C_5)$carbamoylalkyl,
   (viii) $(C_2-C_5)$cyanoalkyl,
   (ix) $(C_3-C_6)$acetylalkyl,
   (x) $(C_7-C_{11})$benzoylalkyl, optionally substituted by one, 2 or 3 chloro, $(C_1-C_3)$alkyl, hydroxy, $(C_1-C_3)$alkoxy, carboxy, $(C_2-C_5)$alkoxycarbonyl, or nitro,
   (xi) pyridyl, optionally substituted by one, 2, or 3 chloro, $(C_1-C_3)$alkyl, or $(C_1-C_3)$alkoxy,
   (xii) $(C_6-C_9)$pyridylalkyl optionally substituted by one, 2 or 3 chloro, $(C_1-C_3)$alkyl, hydroxy, or $(C_1-C_3)$-alkyl,
   (xiii) $(C_1-C_4)$hydroxyalkyl,
   (xiv) $(C_1-C_4)$dihydroxyalkyl,
   (xv) $(C_1-C_4)$trihydroxyalkyl,
   with the further proviso that not more than one of $R_{21}$ and $R_{22}$ is other than hydrogen or alkyl,
  (b) cycloamino selected from the group consisting of pyrolidino, piperidino, morpholino, piperazino, hexamethyleneimino, pyrrolino, or 3,4-didehydro piperidinyl optionally substituted by one or 2 $(C_2-C_{12})$alkyl of one to 12 carbon atoms, inclusive;
  (c) carbonylamino of the formula —$NR_{23}COR_{21}$, wherein $R_{23}$ is hydrogen or $(C_1-C_4)$alkyl and $R_{21}$ is other than hydrogen, but otherwise as defined above,
  (d) sulfonylamino of the formula —$NR_{23}SO_2R_{21}$, wherein $R_{21}$ and $R_{23}$ are as defined in (c), (4) —$CH_2NL_2L_3$, wherein $L_2$ and $L_3$ are hydrogen or ($C_1$-$C_4$)alkyl, being the same or different, or the pharmacologically acceptable acid addition salts thereof when $X_1$ is —$CH_2NL_2L_3$;

wherein $Z_1$ is:
  (1) —$CH_2$—$(CH_2)_f$—$C(R_2)_2$, wherein $R_2$ is hydrogen or fluoro and f is zero, one, 2 or 3,
  (2) trans—$CH_2$—CH=CH—,
  (3) —(Ph)—$(CH_2)_g$—, wherein (Ph) is 1,2-, 1,3-, or 1,4-phenylene and g is zero, one, 2, or 3;

wherein $R_8$ is: hydrogen, hydroxy, hydroxymethyl, —$OR_{10}$ or —$CH_2OR_{10}$, wherein $R_{10}$ is tetrahydropyranyl, tetrahydrofuranyl, or —$C(OR_{11})(R_{12})$—$CH(R_{13})(R_{14})$ wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein $R_{12}$ and $R_{13}$ are alkyl of one to 4 carbon atoms, inclusive, phenyl, phenyl substituted with one, 2, or 3 alkyl of one to 4 carbon atoms, inclusive, or when $R_{12}$ and $R_{13}$ are taken together —$(CH_2)_a$— or when $R_{12}$ and $R_{13}$ are taken together —$(CH_2)_b$—O—$(CH_2)_c$, wherein a is 3, 4, or 5 and b is one, 2 or 3, and c is one, 2, or 3 with the proviso that b plus c is 2, 3, or 4, with the further proviso that $R_{12}$ and $R_{13}$ may be the same or different, and wherein $R_{14}$ is hydrogen or phenyl;

wherein $Y_1$ is: trans—CH=CH—, cis—CH=CH—, —$CH_2CH_2$— or —C≡C—;

wherein $M_1$ is $\alpha$-$OR_{12}$:$\beta$-$R_5$ or $\alpha$-$R_5$:$\beta$-$OR_{12}$, wherein $R_5$ is hydrogen or methyl and $R_{12}$ is hydrogen or methyl, with the proviso that $R_{12}$ is methyl only when $R_5$ is hydrogen;

wherein $L_1$ is $\alpha$-$R_3$:$\beta$-$R_4$, $\alpha$-$R_4$:$\beta$-$R_3$, or a mixture of $\alpha$-$R_3$:$\beta$-$R_4$ and $\alpha$-$R_4$:$\beta$-$R_3$, wherein $R_3$ and $R_4$ are hydrogen, methyl, or fluoro, being the same or different, with the proviso that one of $R_3$ and $R_4$ is fluoro only when the other is hydrogen or fluoro;

wherein $R_7$ is:
  (1) —$(CH_2)_m$—$CH_3$, wherein m is an integer from one to 5, inclusive;
  (2) phenoxy optionally substituted by one, two or three chloro, fluoro, trifluoromethyl, ($C_1$-$C_3$)alkyl, or ($C_1$-$C_3$)alkoxy, with the proviso that not more than two substituents are other than alkyl;
  (3) phenyl, benzyl, phenylethyl, or phenylpropyl optionally substituted on the aromatic ring by one, two or three chloro, fluoro, trifluoromethyl, ($C_1$-$C_3$)alkyl, or ($C_1$-$C_3$)alkoxy, with the proviso that not more than two substituents are other than alkyl;
  (4) cis—CH=CH—$CH_2$—$CH_3$;
  (5) —$(CH_2)_2$—CH(OH)—$CH_3$, or
  (6) —$(CH_2)_3$—CH=$C(CH_3)_2$;
  (7) cyclopentyl, optionally substituted in the 3 position by ($C_1$-$C_4$)alkyl;
  (8) cyclohexyl optionally substituted by ($C_1$-$C_4$)alkyl,
  (9) —$C(R_3R_4)$—$(CH_2)_n$—$CH_2R_{14}$ wherein $R_3$ and $R_4$ are as defined above (in $L_1$), n is an integer from 1 to 4 and $R_{14}$ is hydrogen or 1-4C alkyl;

wherein —$C(L_1)$—$R_7$ taken together is
  (1) cyclopentyl optionally substituted in the 3 position by ($C_1$-$C_4$)alkyl,
  (2) cyclohexyl optionally substituted by ($C_1$-$C_4$)alkyl,
  (3) 2-(2-furyl)ethyl,
  (4) 2-(3-thienyl)ethoxy, or
  (5) 3-thienyloxymethyl.

2. A compound of claim 1 wherein $X_1$ is —$CO_2H$ or —$CO_2CH_3$, $Z_1$ is —$(CH_2)_3$—, and $R_7$ is —$(CH_2)_4$—$CH_3$, —$(CH_2)_3CH_3$, cyclohexyl, cyclopentyl, or substituted cyclopentyl.

3. 9-Deoxo-9-methylene-6-keto-$PGE_1$, methyl ester, a compound of claim 2.

4. 9-Neoxo-9-methylene-6-keto-$PGE_1$, a compound of claim 2.

5. 9-Deoxo-9-methylene-16,16-dimethyl-6-keto-$PGE_1$, a compound of claim 2.

* * * * *

UNITED STATES PATENT OFFICE
CERTIFICATE OF CORRECTION

Patent No. 4,349,690          Dated 14 September 1982

Inventor(s) Gordon L. Bundy

It is certified that error appears in the above-identified patent and that said Letters Patent are hereby corrected as shown below:

Column 12, line 26, "($CCDl_3$;" should read -- ($CDCl_3$; --.
Column 18, lines 1-9, that portion of the formula should appear as follows:

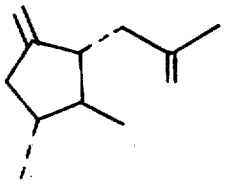

Column 20, line 37, "-Neoxo-" should read -- -Deoxo - --.

Signed and Sealed this

Eighteenth Day of January 1983

[SEAL]

Attest:

GERALD J. MOSSINGHOFF

Attesting Officer      Commissioner of Patents and Trademarks